United States Patent [19]

Hutson

[11] Patent Number: 5,490,516
[45] Date of Patent: * Feb. 13, 1996

[54] METHOD AND SYSTEM TO ENHANCE MEDICAL SIGNALS FOR REAL-TIME ANALYSIS AND HIGH-RESOLUTION DISPLAY

[76] Inventor: William H. Hutson, 47 Grange Ave., P.O. Box 0221, Little Compton, R.I. 02837

[*] Notice: The portion of the term of this patent subsequent to Sep. 20, 2011, has been disclaimed.

[21] Appl. No.: 58,571

[22] Filed: May 6, 1993

Related U.S. Application Data

[63] Continuation-in-part of Ser. No. 991,291, Dec. 15, 1992, Pat. No. 5,348,020, which is a continuation-in-part of Ser. No. 978,245, Nov. 18, 1992, Pat. No. 5,245,587, which is a continuation-in-part of Ser. No. 628,337, Dec. 14, 1990, Pat. No. 5,175,710.

[51] Int. Cl.$^6$ .................................................. A61B 5/0402
[52] U.S. Cl. ............................................ 128/696; 128/901
[58] Field of Search ..................................... 128/696, 698, 128/699, 708, 901; 364/413.06

[56] References Cited

U.S. PATENT DOCUMENTS

| | | | |
|---|---|---|---|
| 3,894,348 | 7/1975 | Fontaine | 35/10.4 |
| 4,422,459 | 12/1983 | Simson | 128/702 |
| 4,458,691 | 7/1984 | Netravali | 128/705 |
| 4,458,692 | 7/1984 | Simson | 128/705 |
| 4,492,235 | 1/1985 | Sitrick | 128/705 |
| 4,630,204 | 12/1986 | Mortara | 364/417 |
| 4,736,199 | 4/1988 | Chadwick et al. | 340/728 |
| 4,839,853 | 6/1989 | Deerwester et al. | 364/900 |
| 4,965,732 | 10/1990 | Roy, III et al. | 364/460 |
| 4,973,111 | 11/1990 | Haacke et al. | 324/309 |
| 4,995,011 | 2/1991 | Spiesberger | 367/127 |
| 5,001,747 | 3/1991 | Sexton | 379/410 |
| 5,010,504 | 4/1991 | Lee et al. | 364/574 |
| 5,031,155 | 7/1991 | Hsu | 367/25 |
| 5,109,863 | 5/1992 | Semmlow et al. | 128/715 |
| 5,175,710 | 12/1992 | Hutson | 367/135 |
| 5,245,587 | 9/1993 | Hutson | 367/100 |

OTHER PUBLICATIONS

Schmidt, "Multiple Emitter Location and Signal Parameter Estimation," *IEEE Transactions on Antennas and Propagation*, vol. AP-34, No. 3, pp. 276-280, Mar. 1986.

Carroll et al., "Models and Methods for Three-way Multidimensional Scaling," Bell Laboratories.

Owsley, "Enhanced Minimum Variance Beamforming," *NUSC Technical Report 8305*, pp. 1-8, Nov. 18, 1988.

(List continued on next page.)

*Primary Examiner*—William E. Kamm
*Assistant Examiner*—Scott M. Getzow
*Attorney, Agent, or Firm*—Hale and Dorr

[57] ABSTRACT

A medical processing and display system that may be used with a medical monitoring device. This system enhances the medical data it receives. Once received, the medical data is reformatted into a two-dimensional matrix, X. A history database and other information are concatenated with the two-dimensional matrix. The concatenated matrix is decomposed using singular value decomposition ("SVD") to obtain corresponding left and right singular vectors, L and R, respectively, and singular values D. Selected singular vectors are transformed to their autocorrelation matrix form, which are concatenated, then decomposed using SVD to their corresponding singular vectors P, P$^t$, and singular values D. Certain of the singular vectors P are selected to filter out signal components of interest. The singular values D of the autocorrelation matrix are modified and used to adjust the weights of the associated singular vectors P. The weighted singular vectors are then combined and the resulting coefficients are used as a FIR filter to enhance the original singular vectors L and/or R$^t$ to enhance singular values $L_e$, $R_e$. Enhanced medical data containing the features of interest $X_e$ is generated from the enhanced original matrix singular values $L_e$ and $R_e$, and modified singular values $D_e$, and the results may be displayed to a diagnotician in various formats.

50 Claims, 7 Drawing Sheets

OTHER PUBLICATIONS

Marple, *Digital Spectral Analysis,* Chapter 13, pp. 362–375, Prentice–Hall, Inc., Englewood Cliffs, N.J.

Kung, "Warp Demo," Department of Computer Science, Carnegie Mellon University, Pittsburgh, Pa., Aug. 29, 1986.

Comon, "An Array Processing Technique Using the First Principal Component," SVD and Signal Processing, pp. 301–316, E. F. Deprettere, Ed., Elsevier Science Publishers B.V., 1988.

Chayka, "Project 96050 Automated Processing of Complex Signal Environments FY86 Final Report," Nov. 1987, MTR–87W00154, The Mitre Corporation.

Weiss et al., "MIT Industrial Liaison Program Report," Oct. 23, 1987, LIDS–P–1673.

Callaerts et al., "On–Line Algorithm for Signal Separation Based on SVD," SVD and Signal Processing, pp. 269–276, E. F. Deprettere, Ed., Elsevier Science Publishers, B.V., 1988.

Moody et al., "QRS Morphology Representation and Noise Estimation Using the Karhunen–Loeve Transform," Massachusetts Institute of Technology, IEEE, 1990 0276–6574/90/000/0269.

Breithardt et al., "Standards for Analysis of Ventricular Late Potentials Using High–Resolution or Signal–Averaged Electrocardiography," *JACC,* vol. 17, No. 5, pp. 999–1006, Apr. 1991.

Winters et al., "A Practical Guide to Signal–Averaged Electrocardiography and Late Potential Analysis," Mount Sinai Medical Center, Division of Cardiology, prepared for Arrhythmia Research Technology, Inc. ©1990.

Simson, "Signal Averaging," *Circulation,* vol. 75 (suppl. III), Apr. 1987, pp. III–69–III–73.

Winters et al., "Signal Averaging of the Surface QRSC Complex Predicts Inducibility of Ventricular Tachycardia in Patients with Snycope of Unknown Origin: A Prospective Study," *JACC,* vol. 10, No. 4, Oct. 1987, pp. 775–781.

Gomes et al., "A New Noninvasive Index to Predict Sustained Ventricular Tachycardia and Sudden Death in the First Year After Myocardial Infarction: Based on Signal–Averaged Electrocardiogram, Radionuclide Ejection Fraction and Holter Monitoring", *JACC,* vol. 10, No. 2, Aug. 1987, pp. 349–357.

Gomes, "Clinical Uses of the Signal–Averaged Electrocardiogram", *CVR&R,* Jun. 1988, pp. 25–28.

Haberl et al., "Top–Resolution Frequency Analysis of Electrocardiogram with Adaptive Frequency Determination", *Circulation,* vol. 82, No. 4, Oct. 1990, pp. 1184–1192.

METHOD AND SYSTEM TO ENHANCE MEDICAL SIGNALS FOR REAL-TIME ANALYSIS AND HIGH-RESOLUTION DISPLAY

BACKGROUND OF THE INVENTION

This application is a continuation-in-part of U.S. Ser. No. 07/991,291, now U.S. Pat. No. 5,348,020, filed Dec. 15, 1992 and entitled "A Method and System for Near Real-Time Analysis of Electrocardiograph Signals", which is a continuation-in-part of U.S. Ser. No. 07/978,245, now U.S. Pat. No. 5,245,587, filed Nov. 18, 1992 and entitled "Multi-Dimensional Signal Processing and Display", which is a continuation-in-part of U.S. Ser. No. 07/628,337, filed Dec. 14, 1990, now U.S. Pat. No. 5,175,710, issued Dec. 29, 1992. The above-referenced patent and patent applications are hereby incorporated by reference.

The invention relates to the analysis of various types of medical data signals, including: electrocardiography (ECG) data; electroencepholography (EEG) data; conventional radiographic data; fluroscopy data; angiography data, including cine-loops (e.g. motion pictures); echocardiography data, including ultrasound data; phonocardiography; conventional computed tomography (CT) and ultrafast computed tomography (UFCT) data, including cine-loops; magnetic resonance imaging (MRI) data, including multi-slice, 3D analysis; MRI spectroscopy (MRIS) data; positron emission tomography (PET) data; single positron emission computer tomography (SPECT) data; and other data signals obtained using medical monitoring apparati which contain information which is representative of a subject's medical condition. These data signals may contain both normal medical characteristics and abnormal medical characteristics. Some of the data of particular interest to the diagnostician may be subtle and difficult to discern from other signal components that are received, along with interference and noise. Numerous types of medical signal data are generated in the normal course of medical test procedures, and the present invention allows these data to be analyzed more effectively than is currently possible.

Medical diagnosticians often rely upon computer-assisted techniques to sort through acquired medical signal data to determine the presence or absence of significant characteristics in the data. In U.S. patent application Ser. No. 07/991,291, "A Method and System for Near Real-Time Analysis of Electrocardiograph Signals", a method to separate and isolate ECG components from dominant heartbeat patterns, interference and noise is described. Other medical signals may be isolated and enhanced in a similar manner. The technique described in U.S. patent application Ser. No. 07/991,291, however, results in empirically-derived signals that may still contain a certain degree of noise, artifacts and other interference. Therefore, a data processing system that can further isolate and enhance medical signals in order to detect and reliably present medically-important signals of interest is required. Medical signals obtained using present monitoring devices contain unwanted components, such as effects due to movement of the patient, respiration effects, AC interference, and other obscuring signals. These components need to be diminished, and the data enhanced before signals of interest in the data can easily be observed for analysis.

The medical diagnostician often may have some prior understanding, or models, of the underlying physical mechanisms, prior history data, or other a priori information which may help guide the interpretation of the new medical data being acquired. Therefore, a data processing system which enables the incorporation of such models, histories and a priori information is necessary to enable the diagnostician to make the best medical diagnosis, based on all pertinent information available.

The present invention is used with data obtained from different medical modalities to reduce noise and unwanted signals and to enhance signals of interest. For example, it is used with ECG data to enhance the heartbeat data, allowing electrical alternans, ventricular late potentials, and other diagnostically important features in the heartbeat signals to be detected. It is used to isolate and enhance waveform structures and to improve the isolation, identification and localization of features in electroencepholograph (EEG) data. The system of the present invention improves the contrast, reduces noise, and enhances edges of conventional radiographic data. It improves wall-motion displays and enhances 3D cine-loop displays of fluoroscope and angiograph data. When used with echocardiograph data, B- and M-scan data may be correlated, or data fused, and cine-loops may be enhanced, compressed, transmitted and displayed. The present invention improves the spectral resolution of both conventional computed tomography (CT) and ultrafast computed tomography (UFCT) data, and allows for rapid "deblurring," back projection and inversion of the data for image reconstruction, as well as cine-loop enhancement. It improves the resolution, enhances contrast, reduces noise, and enhances cine-loop retrieval and display of magnetic resonance imaging (MRI) data. When used with MRI spectroscopy (MRIS) data, positron emission tomography (PET) data, or single photon emission computer tomography (SPECT) data, spectral resolution is improved and contrast is enhanced. It also enables real-time data fusion of EEG and SPECT data.

In prior art medical systems, a technique of signal averaging is frequently used to reduce the effect of random noise. However, noisy data not only include random, noise-like components, but may also contain non-random, signal-like components, such as unwanted features in the data and AC interference. While signal averaging reduces noise, it does not reduce these non-random, signal-like, components. Unfortunately these unwanted components may obscure and interfere with the recognition of weak signals of interest.

It is therefore an object of the present invention to provide a real-time medical analysis system that will more accurately separate and isolate signal components of interest from predominant, yet unwanted features, interference, and noise.

It is also an object of the present invention to provide a medical analysis system to process medical data which does not require special sensors or additional sophisticated equipment, but may be used within or in conjunction with commonly-used sensor systems.

It is a further object of the present invention to provide a medical analysis system that isolates and enhances important signal patterns, analyzes the patterns using high-resolution computational techniques, and displays the results in multiple display formats.

It is also an object of the present invention to provide a medical analysis system that processes medical data more rapidly, using smaller data samples, yet resulting in higher precision, than is available using current systems.

It is also an object of the present invention to enable medically-based models, historic data and other a priori information to be incorporated in the enhancement process to improve subsequent analysis and interpretation of the medical data.

It is also an object of the present invention to provide a medical analysis system that will project analytical results back into the original sample space or into other spatial domains, thus permitting a diagnostician to conveniently view the features of interest in the data in various forms and formats.

It is also an object of the present invention to enhance and store data in a compressed form, transmit the compressed data, and then rapidly retrieve and display the data from multiple perspectives, and to display the data as a movie replay of medically-important features moving within a three-dimensional, transparent data cube, or portions of a higher-dimensional hypercube.

SUMMARY OF THE INVENTION

In the preferred embodiment, the multi-dimensional medical processing and display system of the present invention is used with an existing medical monitoring and imaging system to reduce noise and unwanted signals and to enhance signals of interest in medical data. The medical system provides data, obtained from one or more sensors, to the processing system. As the data is collected, it is arranged into a matrix. The dimensions of the matrix vary depending upon the form of the data, from one dimension, up to any number of multiple dimensions.

The medical data, obtained from a particular medical monitoring device such as an ECG monitor, a phonocardiographic monitor, EEG monitor, conventional radiographic equipment, a fluoroscopic system, angiographic system, echocardiographic system, an ultrasound device, as well as CT, UFCT, MRI, MRIS, PET, or SPECT systems, or other medical devices, could inherently be comprised of one, two, three, or higher-dimensional data. The data are reformatted by the present invention into a single two-dimensional matrix X. When data of three or higher dimensions are obtained, the data are separated into multiple two-dimensional matrices, which are then concatenated along a common dimension, forming one large two-dimensional matrix. When data that are inherently one-dimensional is obtained, they are segmented and reformatted into a two-dimensional matrix. In addition, multiple medical modalities may be correlated, "data fused", or processed simultaneously, including data fusion of M-scan, B-scan and doppler data in ultrasound; data fusion of ECG and B-scan ultrasound; data fusion of ECG and phonocardiograph data; and data fusion of EEG waveforms and SPECT.

Once the data is in the form of a single two-dimensional matrix X, a historic database and other a priori information, such as a compressed form of modelled medical data, or otherwise anticipated results, is concatenated with the two-dimensional matrix. These data allow interfering signals and noise in the data to be diminished and other signals of interest to be enhanced. The data are then analyzed efficiently using singular value decomposition (SVD). The two-dimensional, concatenated matrix X is decomposed to obtain a compressed and enhanced form of the data matrix. In the preferred embodiment, the data matrix X is decomposed to obtain its corresponding left and right singular vectors L, R and singular values D. The singular vectors are partitioned into one or more groups, or subspaces, either on the basis of their corresponding singular values, by evaluating their singular vectors, or by some other criteria.

After the singular values and singular vectors have been partitioned into subspaces, singular vectors from one or more subspaces are selected for further processing to enhance features of interest and to remove noise and other unwanted signal components.

In one embodiment, the selected singular vectors are transformed into their Hankel matrix form, concatenated together, then decomposed using singular value decomposition. The resulting left singular vectors P are transformed into their frequency domain representations by the Fast Fourier Transform (FFT), or related spectral techniques, for further analysis. The corresponding right singular vectors Q represent features within the original signal which have been adaptively filtered, or otherwise modified, to enhance and display signal components of interest and may be analyzed further as well.

This analysis enables the results to be classified into subspaces with the intent of retaining and further enhancing those singular vectors associated with features of interest and reducing or eliminating those singular vectors which are associated with interference, noise, or other unwanted components.

In an alternative embodiment, the autocorrelation matrix is calculated by reformatting the singular vectors into their Hankel matrix form H, then calculating the cross-product matrix $HH^t$ (or alternatively $H^tH$).

In the preferred embodiment, the autocorrelation matrix of each singular vector is computed by first taking the Fast Fourier Transform (FFT) of the singular vectors, then multiplying the results by their complex conjugate, and then transforming the results back the Inverse FFT (IFFT). The resulting autocorrelation function is then formatted to its Toeplitz matrix form A by placing multiple copies of the function in a matrix, with each copy offset at equal intervals to the right.

After the autocorrelation matrix A is calculated, it is decomposed into its corresponding singular vectors P, $P^t$ and singular values D. In an alternative embodiment, the autocorrelation matrix is decomposed using eigenanalysis into its corresponding eigenvalues and eigenvectors. The resulting singular vectors P (or eigenvectors) are separated into subspaces.

Certain of the autocorrelation singular vectors P are selected to filter out signal components of interest from singular vectors L, $R^t$, which represent unwanted components, such as AC interference and noise. To further enhance the selected components of interest, the singular values D of the autocorrelation matrix are modified and used to adjust the weights of the associated singular vectors P. The weighted singular vectors are then combined and the resulting coefficients are used as a Finite Impulse Response (FIR) filter to enhance the original singular vectors L and/or $R^t$ into enhanced singular values $L_e$, $R_e$.

Enhanced medical data containing features of interest $X_e$ is then generated from the enhanced original matrix singular values $L_e$ and $R_e$, and modified singular values $D_e$, and the results may be displayed to the diagnostician in various formats. $L_e$, $R_e$ and/or $X_e$ may be thresholded to improve subsequent visualization and data analysis.

All or portions of the enhanced data $X_e$ is then displayed. The enhanced data is rotated and displayed from different perspectives. When three-dimensional data is displayed, the rotation is efficiently achieved by first rotating the singular vectors to the appropriate angle, then expanding only that portion of the full dataset which will be visible. With this rotation of the compressed singular vectors, rather than the full, three-dimensional dataset, the amount of required computations are substantially reduced.

BRIEF OVERVIEW OF THE DRAWINGS

Other objects, features, and advantages of the invention will become apparent from the description of a particular embodiment, taken in combination with the drawings, in which:

FIG. 9c is the Subspace-Enhanced form of the singular vector of FIG. 9a;

DETAILED DESCRIPTION OF A PREFERRED EMBODIMENT

Figure 1A:
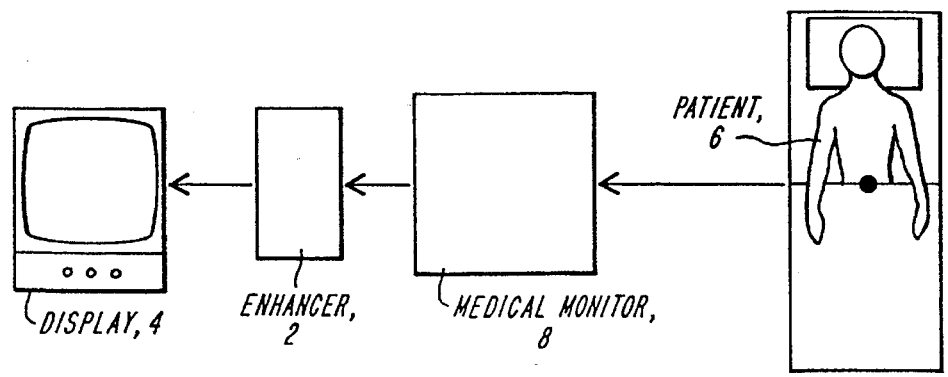
FIG. 1A shows the enhancer system of the present invention in use with a medical monitoring system.

Referring to FIG. 1A, the enhancer system 2 of the present invention improves the quality of medical data that is collected from a patient 6 using a medical monitoring system 8. The enhancer system 2 either may be built into a medical monitor or may be added to an existing medical monitor 8. The enhancer 2 reduces or eliminates unwanted data, such as background noise, AC interference, effects of respiration, and unwanted dominant features, and also enhances various features in the medical data, which are displayed to the diagnostician on display 4.

The present invention may be used with medical data obtained from various types of medical monitoring devices, and is not limited to any particular device. The system reduces noise and enhances signals of interest in the particular data being analyzed. When used with ECG data obtained from an ECG monitor, a medical diagnostician can focus in on features of interest in the ECG data such as electrical alternans, ventricular late potentials, or other important features. When used with phonocardiographic monitoring of the heart, it may be used to isolate and localize abnormalities in the heart valve function, including stenosis, mitral valve prolapse, etc. It isolates and enhances the waveform structures in the data and improves signal localization in EEG data. The system improves contrast resolution, edge enhancement, noise reduction and the display of conventional radiographic data. It improves wall motion displays, 3D cine-loop motion enhancement and other displays of fluoroscopic and angiographic data; it correlates or fuses B- and M-scan echocardiographic data, and enhances the cine-loop, data compression, transmission and display of the data. It data fuses ECG and phonocardiographic data. The system improves the spectral resolution, image reconstruction, projection and rotation, as well as cine-loop enhancement, of conventional CT and UFCT data. It improves the resolution, enhances the contrast, reduces noise, and enhances the cine-loop retrieval in the display of MRI data. The present invention improves the spectral resolution of MRIS data as well as improving the resolution, enhancing the contrast, and aiding in image reconstruction using PET and SPECT data. It enables the simultaneous correlation of EEG waveforms and SPECT data.

Figure 1:
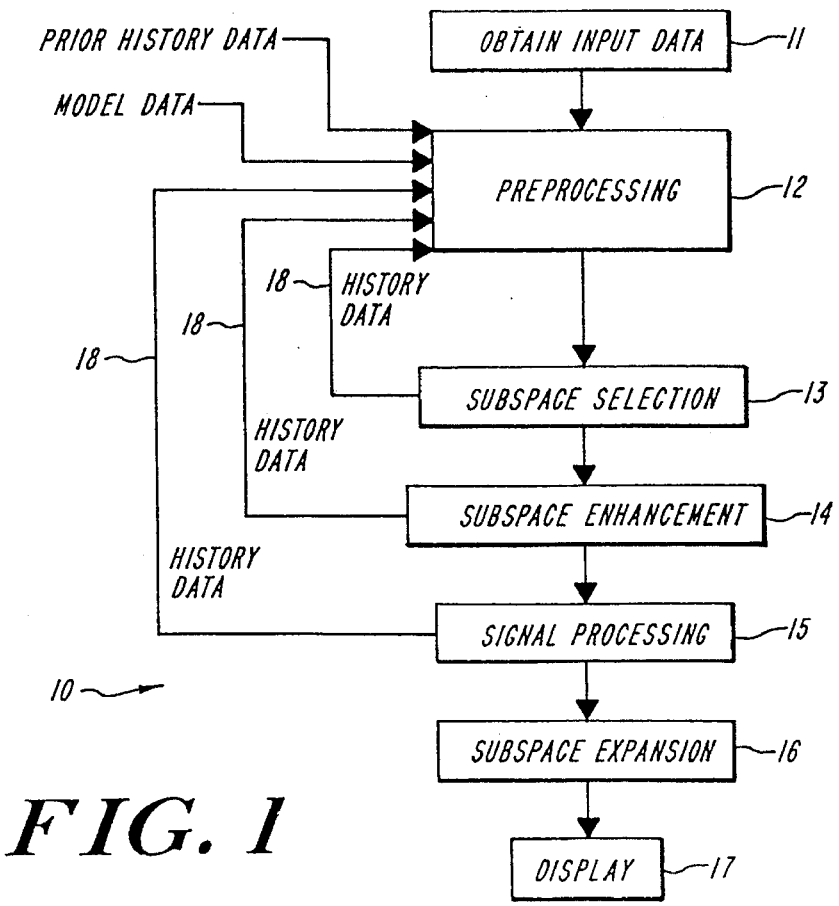
FIG. 1 is a flow chart for the main algorithm of the preferred embodiment of the present invention.

Referring to FIG. 1, a flow chart for the main algorithm 10 of the present invention is shown. Initially, medical input data 11 is received from a medical monitoring system, and is pre-multiplied, weighted and reformatted into a single two-dimensional matrix by Preprocessing Function 12.

The Subspace Selection Function 13 compresses and refines the medical data in the two-dimensional data matrix. The data matrix is compressed by decomposing it into its singular values D and singular vectors L and R. The data are refined by modifying or eliminating some of the singular values in D. In this manner, unwanted features, interference, and noise are suppressed and/or eliminated from the data. The Subspace Selection Function selects a subset of the compressed and refined data for further processing.

Subsequent processing is performed on the subset of singular vectors, rather than on the entire set of raw data, resulting in a substantial reduction in the overall processing load of the subsequent stages of processing. The selected subset, in the form of refined left and right singular vectors L, $R^t$, and singular values D are passed from the Subspace Selection Function 13 to the Subspace Enhancement Function 14 for further processing.

The Subspace Enhancement Function 14 converts each selected singular vector L, and/or $R^t$ into an autocorrelation matrix A. The autocorrelation matrix A is decomposed into singular vectors P and singular values E. Because A is symmetric, the left and right singular vectors are equivalent. The results are partitioned into subspaces, and selected subspaces are used to filter the original singular vectors L and/or $R^t$ to further eliminate undesirable features and further refine features of interest.

The Signal Processing Function 15 analyzes selected singular vectors $L_e$, $R^t_e$ to further enhance signal components of interest. The left and right singular vectors $L_e$ and $R^t_e$, which represent the adaptively filtered waveforms, may also be modified to enhance and display signal components of interest for example, through thresholding. The singular values D within each of the groups of singular vectors $L_e$, $R^t_e$ are also modified to form $D_e$, to enhance certain features of interest in the data and to diminish other, unwanted features within the data.

The Subspace Expansion Function 16 generates an enhanced data matrix $X_e$ from $L_e$, $D_e$ and $R^t_e$.

As the compressed and enhanced numerical data is passed in a forward direction through these functions, history data 18 is simultaneously passed backwards from the Subspace Selection Function 13, the Subspace Enhancement Function and/or the Signal Processing Function to the Preprocessing Function 12 to assist in data refinement and monitoring features of interest.

The Preprocessing Function

Figure 2:
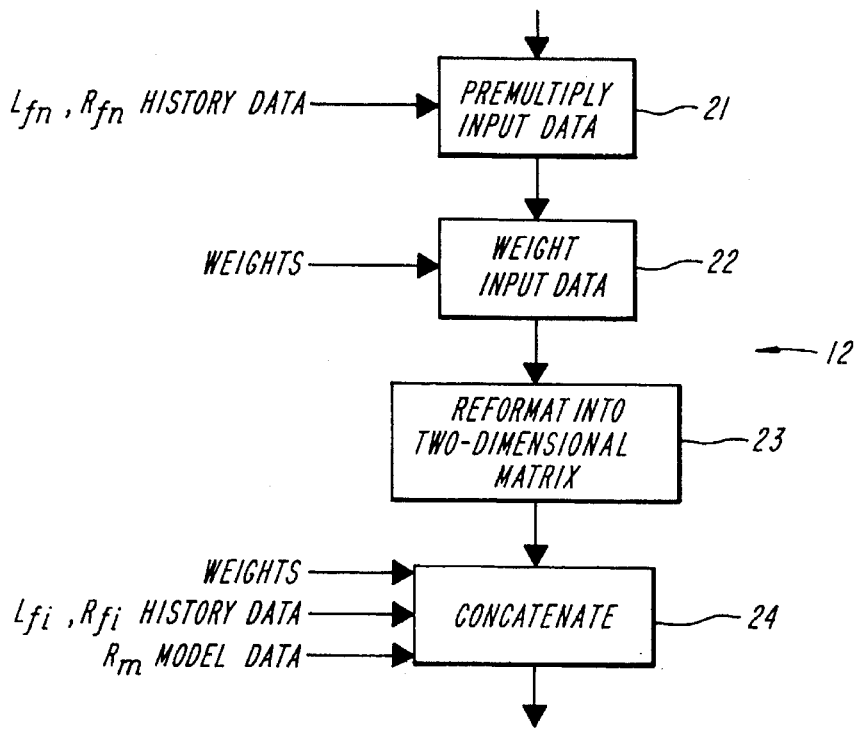
FIG. 2 is a flow chart of the Preprocessing Function.

FIG. 2 shows the Preprocessing Function 12 in greater detail. The Preprocessing Function 12 premultiplies, weights and reformats the medical input data received from a medical monitoring system and concatenates the reformatted data with history data and model-based data.

In the preferred embodiment of the present invention, the input data is prefiltered at 21 by premultiplying the input data by selected history data $L_{fn}$, $R_{fn}$ representing features not of interest in the data. Prefiltering removes unwanted signal components and thereby emphasizes other signal components of interest. The history data is in the form of selected singular vectors which have been passed back from the Subspace Selection Function 13, the Subspace Enhancement Function 14 and the Signal Processing Function 15.

The history data singular vectors representing data not of interest $L_{fn}$, $R_{fn}$ are used to remove selected features not of interest from the input data, such as artifacts due to respiration. For example, new medical data received at time 1 ($X_{t:1}$) is premultiplied by the transpose of $L_{efn}$, then expanded by premultiplying by $L_{efn}$ and subtracting the result from $X_{t:1}$, yielding $Xr_{t:1}$:

$Xr_{t:1} = X_{t:1} - L_{efn}(L^t_{efn} X_{t:1})$, or alternatively through mathematical identities, $Xr_{t:1} = (I - L_{efn} L^t_{efn}) X_{t:1}$, where I is the identity matrix.

In other embodiments, it may be computationally more efficient to enhance the raw input data by postmultiplying the raw input data by previously determined right singular vectors $R^t_{efn}$:

$Xr_{t:1} = X_{t:1} - (X_{t:1} R_{efn}) R^t_{fn}$, or alternatively $Xr_{t:1} = Xr_{t:1}(I - R_{efn} R^t_{efn})$.

In this manner, features not of interest are suppressed or removed from the input data in an initial pass by the Preprocessing Function.

The Preprocessing Function weights the input data at 22 by predefined weights 25 to accentuate or suppress raw data at certain locations in the raw data matrix. Each data value has a weight value for each dimension. For example, in three-dimensional data such as ultrasound, each data value has three weight coefficients. The first coefficient $x_i$ scales the data in the x dimension, the second $y_j$ scales the data in the y dimension, and coefficient $z_k$ scales it in the z-dimension. Similarly, one dimensional data has one vector of associated coefficients, two dimensional data has two vectors of associated coefficients, and higher dimensional data has the appropriate number of additional vectors of coefficients required to scale the data along the other dimensions.

Increasing the magnitude of data at selected locations in the input data increases the importance of the associated data in subsequent analyses, while decreasing the magnitude of raw data at other selected locations similarly decreases the importance of the associated data in subsequent analyses. The weight coefficients can either be preset, set by an automatic function, or interactively altered by the diagnostician.

For example, a diagnostician examining ultrasound data may be particularly interested in the data that corresponds to an organ or structure located a certain distance into the body and not interested in data that corresponds to distances beyond the structure. In such a case, the diagnostician would indicate that the weights corresponding to the distance of particular interest should be increased, and all weights corresponding to distances on either side of the structure should be decreased. The system would then set the distance weights accordingly.

After being appropriately weighted, the input data is reformatted from its original format into a two-dimensional matrix (shown at 23). The medical data, such as ECG, phonocardiograms, EEG, conventional radiography, fluoroscopy, angiography, echocardiography, ultrasound, conventional CT, UFCT, MRI, MRIS, PET, SPECT, other types of medical data, or combinations of the data, that are obtained from a particular medical monitoring device, could be inherently 1-, 2-, 3- or higher-dimensional data. According to the present invention, whatever its original format, the data is reformatted into a two-dimensional matrix. When data of three or higher dimensions is obtained, the data is separated into multiple two-dimensional matrices, which are then concatenated along a common dimension, forming one large two-dimensional matrix. When data that is inherently one-dimensional is obtained, it is first segmented and then reformatted into a two-dimensional matrix.

For example, ECG data obtained from a single sensor lead is inherently one-dimensional data, the single dimension being time. The data is reformatted by collecting it and segmenting it into individual heartbeats, which include the P-, QRS- and T-waves. The individual heartbeats are then arranged as rows of a matrix, resulting in two-dimensional data, one dimension being heartbeat waveform and the other time history.

When the data obtained is three-dimensional, such as data from an ultrasound monitor having dimensions distance into the body, vertical angle, and horizontal angle, the three-dimensional data is separated into multiple two-dimensional matrices, one for each of the measured distances, for example each matrix having dimensions vertical angle by horizontal angle. These matrices are then concatenated together along a common dimension, such as horizontal angle, to form a concatenated two-dimensional matrix having horizontal angle in one dimension and a combination of vertical angle and distance in the other dimension. In other embodiments, the three-dimensional data may be reformatted into two-dimensional form in other ways.

In conventional radiography, fluoroscopy, angiography, B-scan (or M-scan) ultrasound, MRI and PET, the data are inherently 2-dimensional, generally having sagittal and transverse dimensions. When M-scan or B-scan ultrasound data are collected, the data are also inherently 2-dimensional, generally having sagittal and temporal dimensions. When MRIS data are collected, the data are also inherently two-dimensional, generally having the dimensions spectral frequency and time. In phonocardiology, the data are inherently two-dimensional, generally having dimensions time by frequency. However, in multiple sensor phonocardiology, the data are inherently three-dimensional, generally having dimensions time by frequency by location.

When CT, UFCT, MRI and SPECT data (with cine-loop processing) are collected, the data are inherently 3-dimensional, usually having the dimensions sagittal, transverse, and time. In addition, when both M-scan and B-scan ultrasound data are collected, the "fused" data are inherently 3-dimensional, having the dimensions sagittal, transverse and time.

When three-dimensional data such as 3D MRI data is collected over time, this data becomes four-dimensional (X, Y, Z and time). According to the present invention, four-dimensional data is also reformatted into a single two-dimensional matrix. Other modalities may include higher-dimensional data, which are similarly reformatted.

Once the data is in the form of a two-dimensional matrix, the matrix is weighted and concatenated with the history data representing features of interest $L_{fi}$, $R_{fi}$, weights, and model data $R_m$ (shown at 24).

History Data

History data is a special set of medically-pertinent features of interest in the form of right and/or left singular vectors that have been saved in a database. The history database is used when input signals are obtained for more than one time interval, planar slice, or lead. In such a case, the data obtained during each time interval, planar slice, or sensor lead is concatenated with the history data, and the history data is updated at selected intervals.

In the preferred embodiment, the history data singular vectors represent features of interest $R'_{fi}$, $L_{fi}$; features not of interest $R'_{fn}$, $L_{fn}$; enhanced features of interest $R'_{efn}$, $L_{efi}$; and enhanced features not of interest $R'_{efn}$, $L_{efn}$.

The histories of features of interest $R'_{fi}$, $L_{fi}$ are determined, in the preferred embodiment, through analysis of the singular values by the Subspace Selection Function. In alternate embodiments, the features of interest may be determined by analysis of the singular vectors, or by some other criteria either in the Subspace Selection Function, Subspace Enhancement Function or the Signal Processing Function. Selected history data is passed from the Subspace Selection Function to the Subspace Enhancement Function and/or the Signal Processing Function for further data enhancement, resulting in enhanced features of interest $R'_{efi}$, $L_{efi}$.

Referring to FIG. 1, history data of features of interest $R'_{fi}$, $L_{fi}$ are calculated by the Subspace Selection Function 13, the Subspace Enhancement Function 14 and/or the Signal Processing Function 15, and are passed back to the Preprocessing Function 12 to be concatenated with the new medical data. The purpose of this feedback is to enable the energy from weak features of interest to build up to the point where the features of interest may be distinguished from background noise and to improve the description of features not of interest for removal from within the Preprocessing Function.

In alternate embodiments, the history database may be saved and used at a later time to look for changes or differences between it and new medical data. For example, the history database of a mammogram may be saved and compared six months later with a current mammogram to determine changes which may be indicative of cancer.

The history data of features not of interest $R'_{fn}$, $L_{fn}$ are also calculated by the Subspace Selection Function 13 and are fed back to the Preprocessing Function 12 and forward to the Subspace Enhancement Function 14 and to the Signal Processing Function 15. In a similar manner enhanced features not of interest $R'_{efn}$, $L_{efn}$ are fed back from the Subspace Enhancement Function 14 and/or the Signal Processing Function 15 to the Preprocessing Function 12. This information is used to set parameters for further analysis or enhancement and in alternative embodiments may be used to show dominant features in the data (e.g. respiration effects) without obscuring features of interest, or to reconstruct the original data.

The history data is updated at selected time intervals by the Subspace Selection Function, the Subspace Enhancement Function and the Signal Processing Function.

Figure 3:
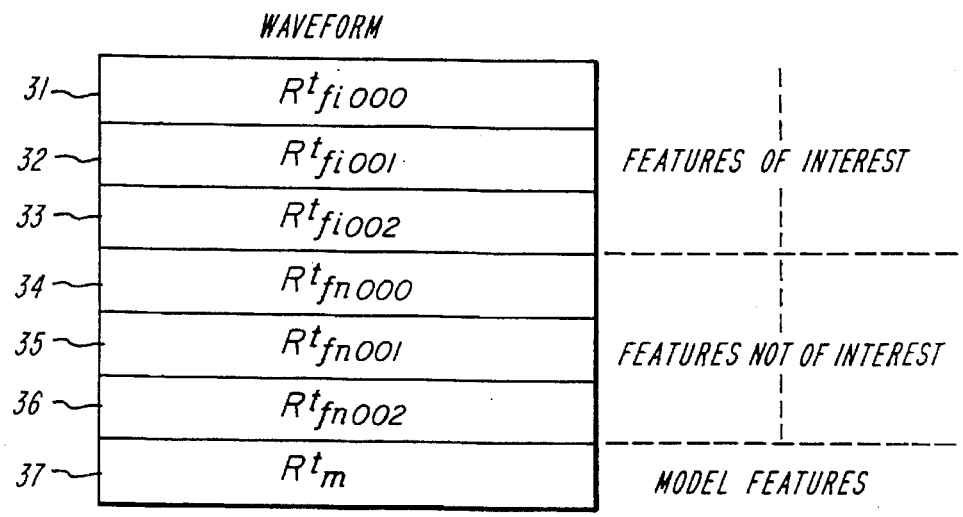
FIG. 3 is the history database for features of interest, features not of interest, and model-based features in the preferred embodiment.

Referring to FIG. 3, a portion of the history database is shown. Right singular vectors representing features of interest $R'_{fi.000}$ 31, $R'_{fi.001}$ 32 and $R'_{fi.002}$ 33 for three time intervals, right singular vectors representing features not of interest $R'_{fn.000}$ 34, $R'_{fn.001}$ 35, and $R'_{fn.002}$ 36 for the same three time intervals, and right singular vector $R'_m$ representing model features similarly stored in the history database 30.

The history database 30 is updated for every time interval, for every planar slice, or every sensor lead, by storing the most recently received history data for right singular vector features of interest $R'_{fi.000}$ 31. At this point, the pre-existing $R'_{fi.000}$ becomes $R'_{fi.001}$ 32 and the pre-existing $R'_{fi.001}$ becomes $R'_{fi.002}$ 33, and so on, to $R'_{fi.nnn}$ where "nnn" corresponds to the length of the compressed time history. The right singular vectors for features not of interest $R'_{fn.000}$ 34, $R'_{fn.001}$ 35, and $R'_{fn.002}$ 36 are similarly stored and updated. The enhanced right singular vectors, left singular vectors, and enhanced left singular vectors are similarly stored in the history database. The history database thus contains historic data that shows the status of the input data for several previous time intervals, planar slices, or sensor leads.

The history database is efficiently maintained in compressed and enhanced form, and represents features of the medical data at various time intervals, planar slices, or sensor leads. Each new analysis includes the compressed and enhanced historical data, which is equivalent to the benefits of a complete analysis of the full (uncompressed) historical data, yet at a fraction of the computational cost.

The compressed history may be efficiently stored for later retrieval, review, analysis and comparison with new medical information. The compressed history database may be quantized, thresholded or otherwise modified for further compression to save storage space. Compression methods well known in the prior art, such as Run Length Coding (RLC), Adaptive Differential Pulse Code Modification (ADPCM), Huffman coding, or other compression techniques, may be used for further compression. The compressed history may be efficiently stored, for example in a "smart card" format for convenience. A "smart card" is a small, portable device such as the size of a credit card, which stores information in volatile RAM, in permanent ROM, or in laser data CDROM format. Such a "smart card" could then be retained in a patient's file or retained and carried by the patient in a credit card or health insurance card format. Alternatively, the compressed medical data may be retained in a central repository for later retrieval, transmission, expansion and analysis.

Model Data

Referring again to FIG. 3, model data is a special set of medically pertinent features of interest in the form of left and/or right singular vectors $R'_m$ which have been predetermined by singular value decomposition of model-based data. In addition, in the Preprocessing function, a priori medical information may be used to guide the weight coefficients of the data to accentuate features of interest. Although singular value decomposition of the new medical data will describe features of interest within the data itself, by concatenating model-based singular vectors, correlations between the new medical data and the model-based data will enhance pertinent features of interest within the new medical data which are correlated with the model-based data. Furthermore, following the singular value decomposition of the concatenated data, the resulting left singular vectors associated with the model-based information $L_m$ will indicate the degree of correlation between the model(s) and the new medical data. In this manner, it is possible to incorporate a number of "alternate models", representing different medical hypotheses or potential diagnoses. The associated coefficients can then be used to evaluate the relevance of the various models to the observed new medical data.

Subspace Selection Function

Figure 4:
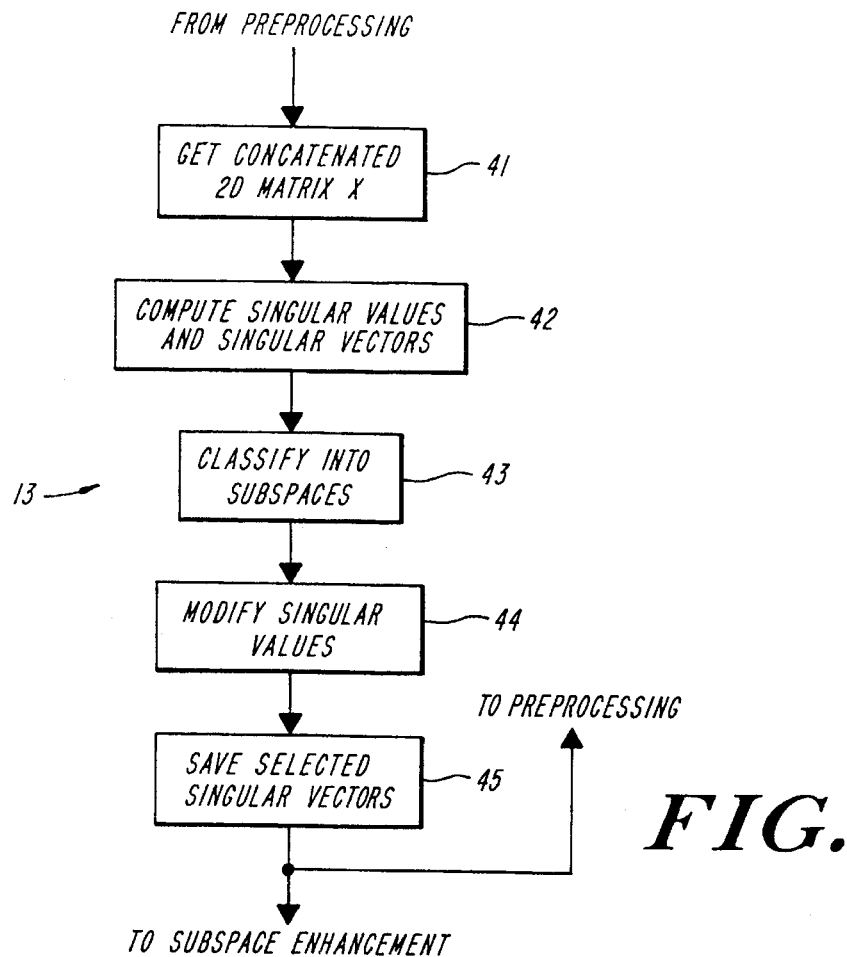
FIG. 4 is a flow chart of the Subspace Selection Function.

Referring to FIG. 4, the Subspace Selection Function 13 is shown in greater detail. The two-dimensional data matrix X, containing the concatenated input data, the history data and the model data, is obtained from the Preprocessing Function (shown at 41). The two-dimensional data matrix X is decomposed using singular value decomposition at 42 to obtain its corresponding singular vectors L, R$^t$ and singular values D. The singular values and singular vectors are used to efficiently describe patterns found in the data.

Matrix analysis using singular values and singular vectors is well known in the prior art. The following publications describe such matrix analysis in detail: *Digital Spectral Analysis with Applications,* S. L. Marple, 1987; *Matrix Computations,* G. H. Golub and C. F. Van Loan, 1989; "Singular Value Decomposition and Least Squares Solutions, "*Numerical Math,* G. H. Golub and C. Reisch, 1970; *LINPAC User's Guide,* J. J. Dongerra, et. al., 1979; and "An Improved Algorithm for Computing Singular Value Decomposition," T. F. Chan, *Communications of the ACM,* 1982.

The left and right singular vectors or sets of singular vectors represent specific characteristics of the data, and, by modifying certain of the singular values and/or singular vectors, selected features within the raw data may be isolated, enhanced, or suppressed. The left singular vectors L correspond to the vertical axis of the data matrix X, and the right singular vectors R correspond to the horizontal axis of the data matrix. The singular values D describe the magnitude of the associated features.

For example, when two-dimensional ECG data is decomposed, the left singular vectors L describe features in the ECG data in terms of their temporal history, while the right singular vectors R$^t$ describe features in terms of their waveform structure. Because electrical alternans, a feature of interest in ECG analysis of ischemia and tachycardia, show up by examining differences between heartbeats over time, they can be detected by analyzing the left singular vectors L. Ventricular late potentials, an indicator of potential tachycardia, however, are detected by examining the waveform structure, represented by the right singular vectors R.

When EEG data is decomposed, the left singular vectors describe features in the data in terms of location or cranial position, while the right singular vectors describe the temporal history and waveform structure, which may be used for analysis of abnormal electrical patterns.

When phonocardiology information is decomposed, the right singular vectors describe features in the data in terms of their frequency composition, while the left singular vectors describe the temporal history of the features. When multi-sensor phonocardiology information is decomposed, the right singular vectors describe features in the data in terms of their frequency composition, while the left singular vectors describe a combination of temporal history and location of the features.

Features in other medical signals, such as those obtained during conventional radiography, fluoroscopy, angiography, B-scan ultrasound, conventional CT, MRI and PET, are similarly found by examining the singular vectors R, L. In such cases, the SVD data compression generally results in vectors that describe essential characteristics of the data in the sagittal and transverse dimensions. When M-scan ultrasound data is analyzed, the SVD data compression represents features of the data in terms of the spectral and temporal dimensions. When UFCT, MRI and SPECT data (with cine-loop processing) is analyzed, the SVD data compression represents features of the data in terms of their sagittal, transverse, and temporal dimensions. In all cases, the singular values D describe the magnitude of the associated features.

The left singular vectors L, right singular vectors R$^t$, and singular values D are thus used to represent important features within the input data, but in a substantially compressed form. This data compression allows the data to be enhanced, further processed, and displayed, without losing any necessary data, but saving substantial amounts of time and computing resources.

In computer tomography, SVD has an added advantage. Because of the orthonormality property of singular vectors, the computationally intensive process of matrix inversion in CT projections such as conventional CT, SPECT and UFCT, may be achieved through a simple matrix multiplication by the transposed singular vectors, thereby greatly reducing the computations involved in tomographic image projection.

For example, in conventional CT it may be necessary to determine the inverse of a matrix R. If R has been decomposed into its singular values and singular vectors, $$R = P_r D_r Q^t_r$$

where r represents the rank of the matrix, then its inverse $$R^{-1} = Q_r D_r^{-1} P^t.$$

Because D is a diagonal matrix, D$^{-1}$ is easily determined by taking the reciprocal of its diagonal elements.

In the preferred embodiment of the present invention, the data processing system uses singular value decomposition to describe patterns, remove unwanted components, and isolate and analyze components of interest in medical data. In alternate embodiments, eigenvector decomposition of the cross-product matrix of the medical data may be used to decompose the medical data. Eigenvector decomposition is also well known in the prior art.

Referring again to FIG. 4, the singular values are classified into subspaces at 43 based on the magnitudes of the singular values or by some other criteria. In the preferred embodiment, singular vectors are classified as one of three general categories: features not of interest (e.g. dominant, yet medically unimportant characteristics such as respiration effects, and effects of AC interference); (2) medical features of interest; and (3) noise. There may be different subspace categories in alternative embodiments. Furthermore, in alternative embodiments, preliminary classification may occur in the Subspace Filtering Function, while further, more sophisticated classification may occur in the Signal Processing Function.

The Subspace Selection Function classifies the singular vectors into subspaces through various means, including: (a) the magnitude of the corresponding singular values; (b) visual display and analysis of either the left and/or right singular vectors; (c) visual display and analysis of the outer product moment of the left and right singular vectors L$_i$ * R$^t_i$, where i is the ith singular vector; and (d) visual display and analysis of the outer product moment of subsets of the left and right singular vector matrices L$_{ss}$ * D$_{ss}$ * R$^t_{ss}$, where ss is a subset of singular vectors.

The data is enhanced at 44 by modifying singular values according to the subspace categories. For example, singular values corresponding to the noise subspace and features not of interest are reduced or set to zero, while the singular values corresponding to the subspace of features of interest remain unchanged or are increased. The data is analyzed in terms of its dominant singular values D and associated left and right singular vectors L, R. The adjustment of the singular values assists in noise reduction, reduction of artifacts and other features not of interest, as well as contrast enhancement of features of interest.

In alternative embodiments of the present invention, singular vectors are rotated using varimax rotation, quartimax rotation, oblique rotation, or other criteria, to maximize their loadings to accentuate data at particular locations in the matrix corresponding to different structures within the body or signals from the body. These operations are well known in the prior art.

The Subspace Selection Function 13 modifies, refines the data, and selects subsets of singular vectors. In the preferred embodiment, a selected set of singular vector history data is passed on to the Subspace Enhancement Function for further processing and analysis of pertinent medical information contained in the singular vectors. The selected set is also saved in the history database to be passed back to the Signal Processing Function for processing and analysis of data in subsequent analyses.

Subspace Enhancement Function

Figure 5A:
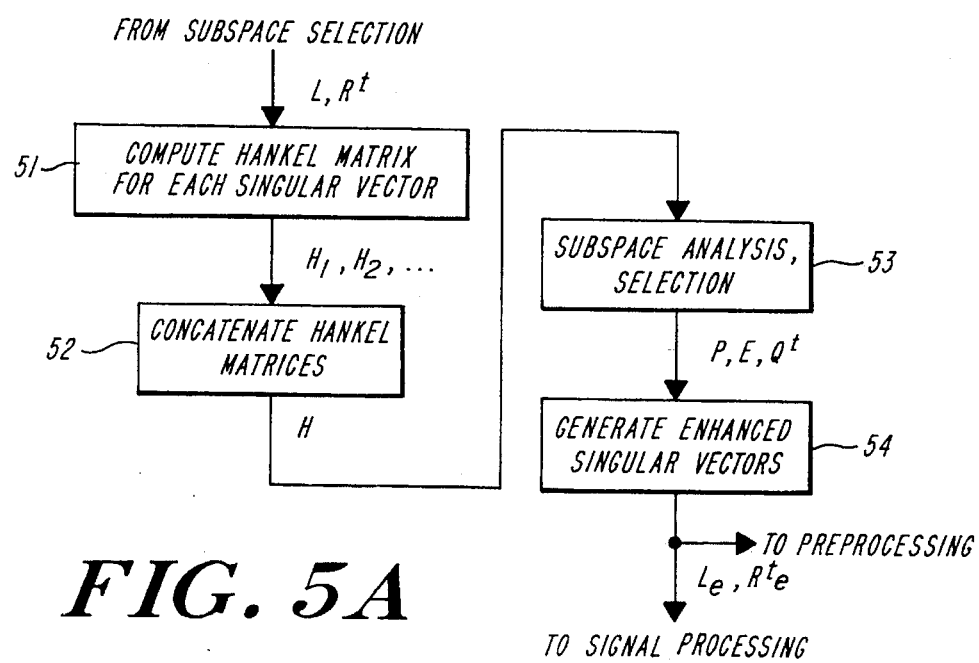
FIG. 5a is a flow chart of an alternative embodiment of the Subspace Enhancement Function.

FIG. 5a is a flow chart showing an alternate embodiment of the Subspace Enhancement Function 14 in greater detail. The Subspace Enhancement Function uses analysis of the autocorrelation function of the singular vectors to reduce the effects of noise and other artifacts and to enhance the contrast of features of interest.

The selected compressed and refined data, in the form of singular vectors L, $R^t$, are passed by the Subspace Selection Function 13 to the Subspace Enhancement Function 14 for further enhancement of medically important indicators within the data. Each of the selected singular vectors L, $R^t$, as received from the Subspace Selection Function, and are analyzed and filtered according to their autocorrelation structure.

Referring to FIG. 5a, in one embodiment, the singular vectors are converted at 51 into their Hankel matrix form. A Hankel matrix is constructed by placing multiple copies of the selected vector in a matrix, with each copy offset to the left one sample, relative to the other copies. After each singular vector is converted to a Hankel matrix, the Hankel matrices are concatenated together at 52 into a single matrix H.

Figure 6:
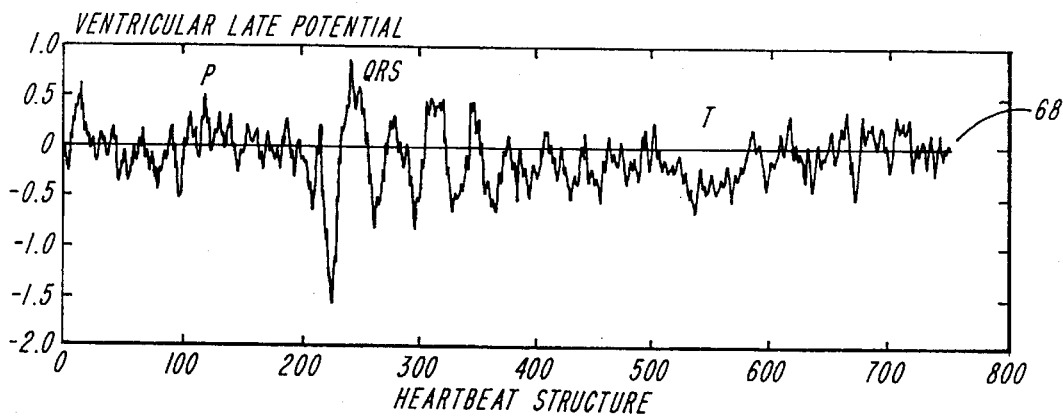
FIG. 6 is a graphic display of a singular vector.
Figure 7:
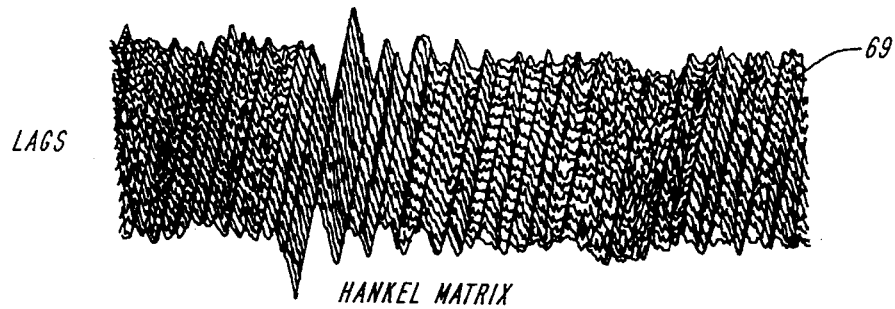
FIG. 7 is the Hankel matrix form of the singular vector of FIG. 6.
Figure 8:
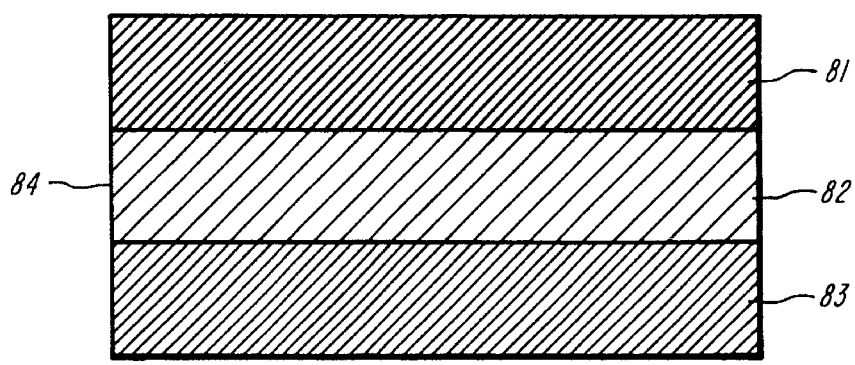
FIG. 8 shows concatentated Hankel matrices.

FIG. 6 shows a singular vector 68. FIG. 7 shows the singular vector 68 transformed into its Hankel matrix form 69, and FIG. 8 shows three Hankel matrices 81, 82, 83 concatenated together to form a single Hankel matrix H 84.

Referring again to FIG. 5a, the matrix H is decomposed using singular value decomposition at 53 into singular vectors P, $Q^t$ and singular values E, although eigenvector decomposition (EVD) of the products $H^tH$ or $HH^t$ could be used interchangeably. The decomposition of H results in three matrices:

P singular vectors which describe autocorrelation characteristics of the data according to their lag structure and represent coefficients for a FIR filter;

$Q^t$ singular vectors which describe the filtered waveform characteristics of the data in terms of the original singular vectors L and/or $R^t$;

E the associated singular values, arranged in decreasing order along the principal diagonal, representing the importance of the features in the original singular vectors.

The Hankel matrix singular vectors P, Q and singular values E are partitioned into subspaces at 53 to eliminate undesirable features, and to further enhance features of interest. Subspace selection may be accomplished through analysis of singular values, analysis of the singular vectors, or other criteria.

Enhanced singular vectors $L_{efi}$, $L_{efn}$ are generated at 54 by combining together selected singular vectors P, which have been weighted by their corresponding singular values E or other criteria:

$$L_{efi} = \Sigma e_i [P_{fi}]_i$$

$$L_{efn} = \Sigma e_i [P_{fn}]_i$$

Figure 5B:
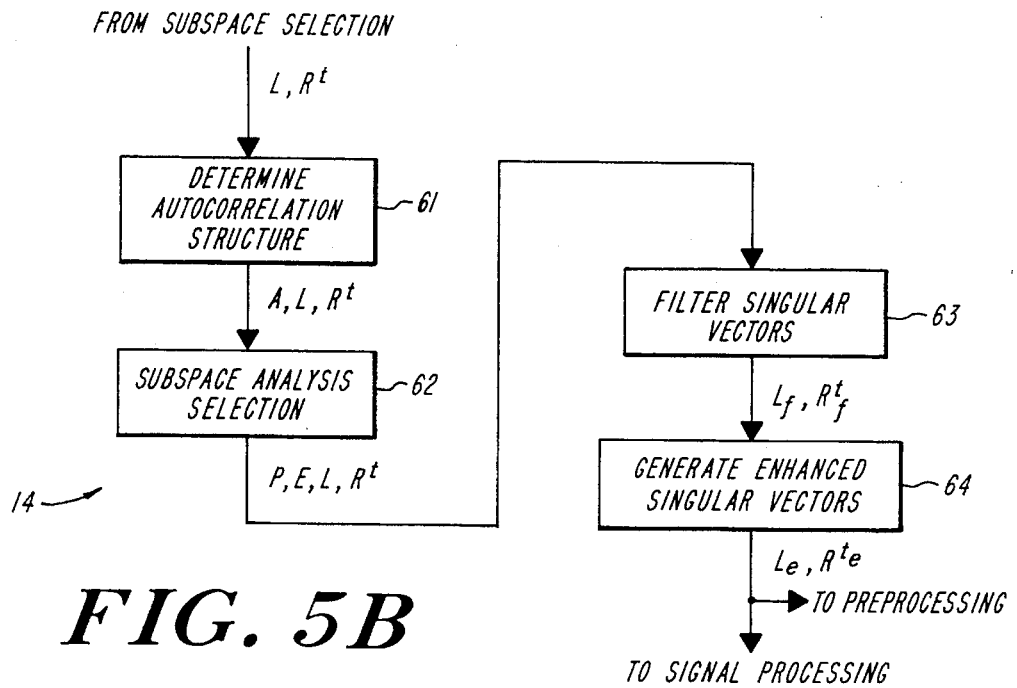
FIG. 5b is a flow chart of the preferred embodiment of the Subspace Enhancement Function.

Referring to FIG. 5b, in the preferred embodiment, the autocorrelation function of each singular vector is calculated using the Fast Fourier Transform (FFT) at 61. First, each singular vector is transformed into the frequency domain using the FFT, then multiplied by its complex conjugate and transformed back into the time domain using the Inverse FFT (IFFT). The resulting autocorrelation function is then placed into its Toeplitz matrix form A.

The autocorrelation matrix A is decomposed using singular value decomposition at 62. The decomposition describes the autocorrelation structures in terms of singular values E and singular vectors P. Selected singular vectors Ps may be used as FIR filter coefficients to filter the original vector (e.g. $R^t$), creating a filtered singular vector $R_f^t$. Generally, a small set of singular vectors describes the dominant structural characteristics of $R^t$. The remaining singular vectors are often related to noise, and thus may be modified, reduced or eliminated.

Enhanced singular vectors $L_{efi}$, $L_{efn}$ are generated at 64 by combining together selected singular vectors P, which have been weighted by their corresponding singular values E or other criteria:

$$L_{efi} = \Sigma e_i [P_{fi}]_i$$

$$L_{efn} = \Sigma e_i [P_{fn}]_i$$

Figure 9A:
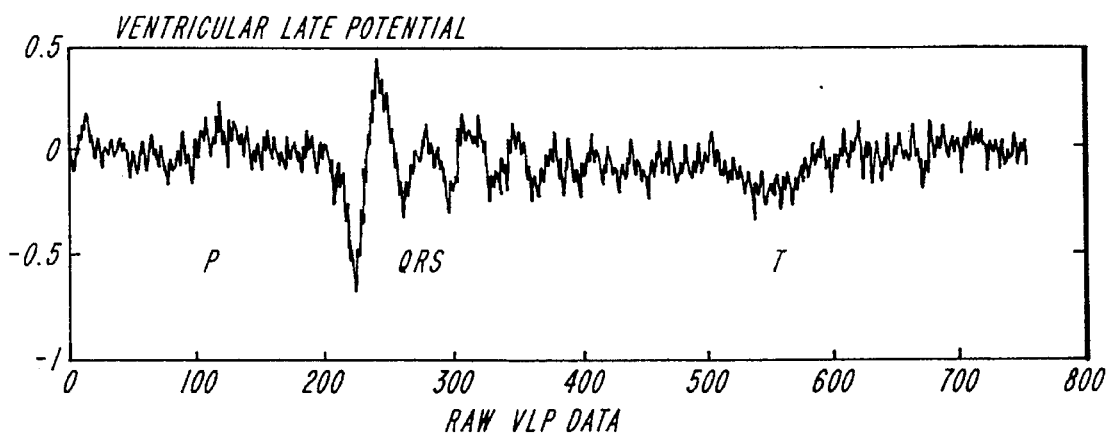
FIG. 9a is a singular vector.
Figure 9B:
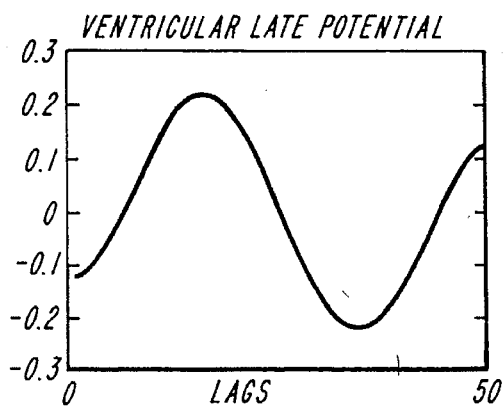
FIG. 9b is a graphic display of Ps, the FIR filter coefficients.
Figure 9C:
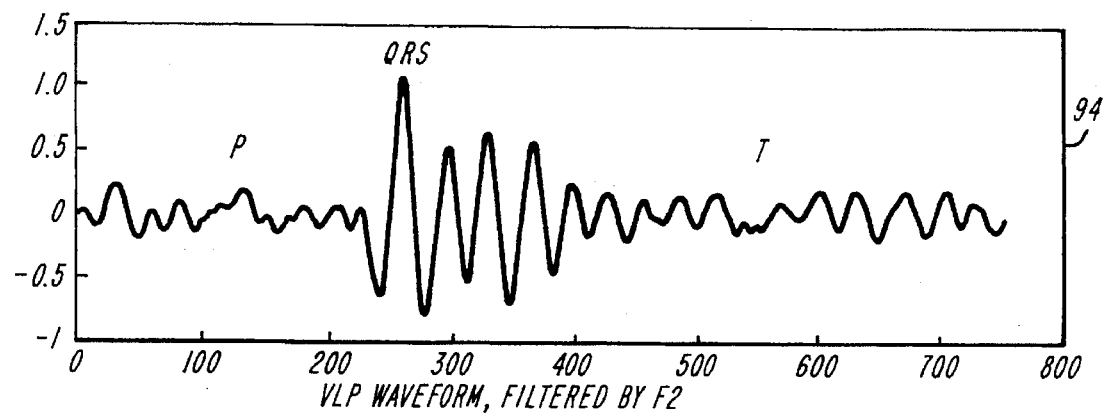

Referring to FIGS. 9a, 9b, and 9c, FIG. 9a is a graphic display of a singular vector, FIG. 9b is a graphic display of Ps, the FIR filter coefficients, and FIG. 9c is the Subspace-Enhanced form of the singular vector $R^t_{efi}$ 94 of FIG. 9a.

Enhanced singular vectors $R^t_{efi}$, $R^t_{efn}$ are generated by combining together selected singular vectors Qt, which have also been weighted by their corresponding singular values E:

$$R^t_{efi} = \Sigma e_j [Q^t_{fi}]_j$$

$$R^t_{efn} = \Sigma e_j [Q^t_{fn}]_j$$

Signal Processing Function

Figure 10:
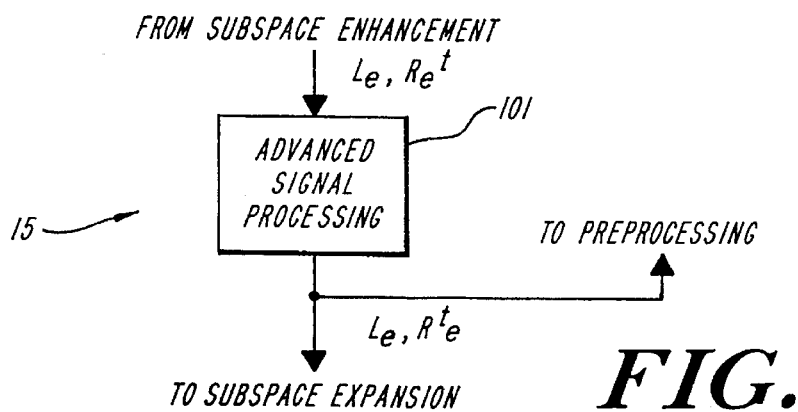
FIG. 10 is a flow chart of the Signal Processing Function.

FIG. 10 shows the Signal Processing Function 15 in greater detail. The compressed and enhanced data, in the form of enhanced singular vectors, $L_e$ and $R^t_e$ are passed from the Subspace Enhancement Function 14 for further analysis.

The singular vectors are subjected to advanced signal processing at 101. Depending upon the type of data, the advanced signal processing could be spectral processing (e.g. for ECG data), spectral-temporal processing (e.g. for phonocardiographic data or MRIS data), or inverse solution (e.g. for CT image projection and reconstruction). Alternatively, in CT, the singular vectors are convolved for "deblurring" purposes, then subsequently expanded through the technique of back projection.

Although all of these types of advanced signal processing are well-known in the prior art, in the present invention, advanced signal processing techniques operate on compressed and enhanced singular vectors $L_e$, $R^t_e$ rather than on raw data. For example, in ECG analysis, Fourier techniques may be used to identify electrical alternans through analysis of $L_e$ and/or ventricular late potentials through analysis of $R_e^t$. In phonocardiology, Fourier techniques may be used to identify abnormalities in the function of heart valves. In ultrasound analysis, matched filter processing of singular vectors and modification of singular values may be used to enhance the form and contrast resolution of weak, yet medically important features. In CT processing, the singular vectors may be convolved for the purpose of "deblurring", then processed further to generate back projections of internal structures. In the present invention, the input to the Signal Processing Function is in the form of enhanced singular vectors $L_e$, $R_e^t$, rather than raw input data. By diminishing or eliminating certain singular vectors, features not of interest, such as AC interference, may be suppressed or removed, resulting in greater performance.

Subspace Expansion Function

Figure 11:
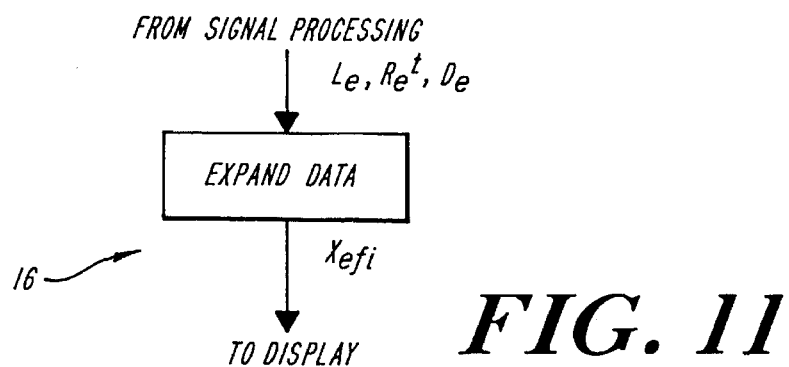
FIG. 11 is a flow chart of the Subspace Expansion Function.

FIG. 11 shows the Subspace Expansion Function 16 in greater detail. The compressed and enhanced data is obtained from the Signal Processing Function. Presentations of enhanced features of interest $X_e$ in the data are generated by the multiplication of the enhanced left singular vectors $L_e$, modified singular values $D_e$, and the enhanced right singular vectors $R_e^t$:

$$X_e = L_e D_e R_e^t,$$

Display Function

Referring again to FIG. 1, after data expansion, the enhanced data $X_{efi}$, $X_{efn}$ is displayed by the Display Function 17. The data, which has been enhanced and/or thresholded, is displayed so that features that occur in the data are displayed in the format in which they appear inherently in the data.

In the preferred embodiment of the present invention, the two-dimensional concatenated matrix is reformatted back into its original form. Three-dimensional data is displayed as a three-dimensional data cube. Four-dimensional data is displayed using color in the three-dimensional cube. With thresholding, features of interest are displayed in the form of opaque objects within an otherwise transparent cube on an operator interface screen. Features not of interest may similarly be displayed in a separate display. The operator can interactively rotate the three-dimensional transparent cube through various angles and display the data from different perspectives. This type of display is not possible in prior art systems which do not eliminate interference and noise, nor correlate enhanced data across all dimensions.

Figure 12A:
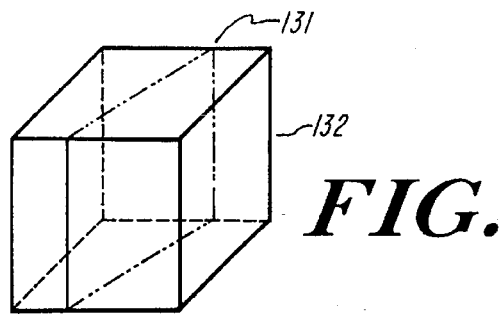
FIGS. 12a–12d show rotation and display of the three-dimensional data cube through rotation of singular vectors.
Figure 12B:
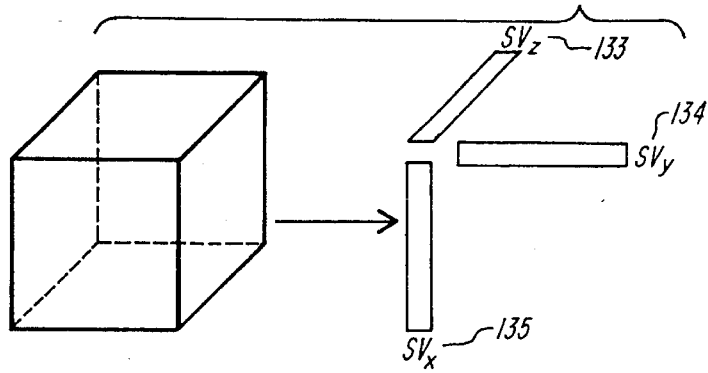
Figure 12C:
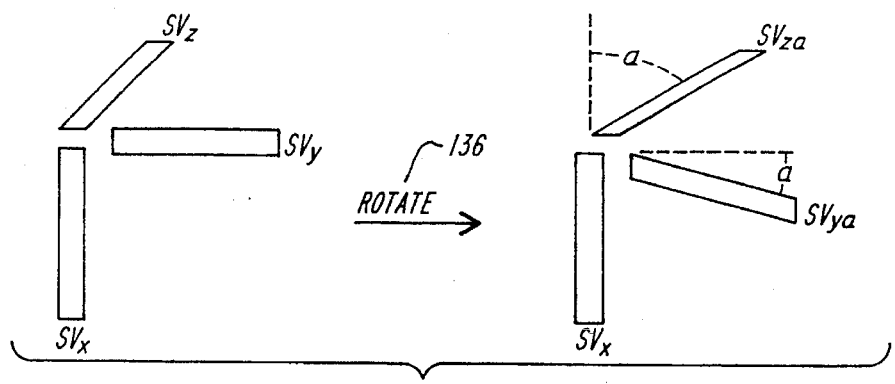
Figure 12D:
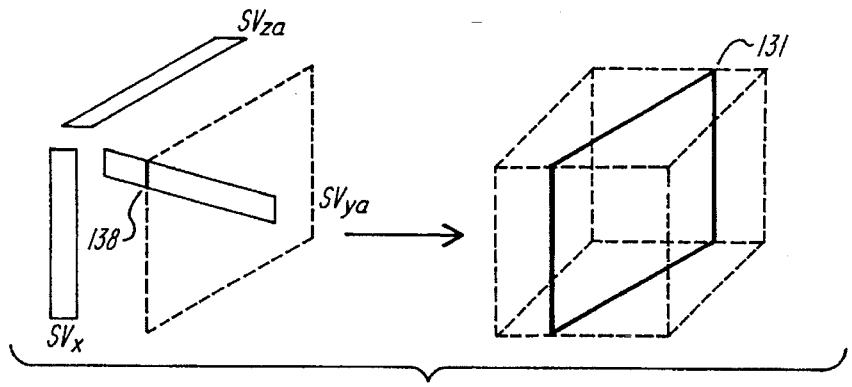

Referring to FIGS. 12a, 12b, 12c and 12d, in the case of three-dimensional data, rotation is achieved more efficiently by rotating the singular vectors, rather than the full enhanced dataset $X_{efi}$. To obtain the perspective view of data 131, shown in the datacube 132, the singular vectors 133, 134, 135 of the original data cube 132 are rotated through the appropriate angles a (and/or b) 136 (e.g. rotating the singular vectors $SV_{ya}$=cos (a) $SV_y$ and $SV_{za}$=cos (a) $SV_z$, as shown in FIG. 12c). Only those portions of the full dataset 131 which will be visible are then expanded. Referring to FIG. 12d, to generate the perspective view 131, the singular vector $SV_x$ would first be multiplied by the appropriate scalar value $SV_{ya(i)}$ 138, then expanded into its full two-dimensional form by postmultiplying by the transpose vector $SV_{za}^t$. With the prior rotation of singular vectors, considerable computations may be saved, as contrasted to the rotation of the full, three-dimensional dataset.

The screen display includes cursors for each of the dimensions of the data, which together allow a diagnostician to freely "travel" through the cube, displaying any desired data at any time. In addition, the diagnostician can use these cursors to control the display of "slices," or planes, through the data.

The diagnostician can display these slices, or planes, in the three-dimensional data cube using a set of multiple planar displays. In alternative embodiments of this format, the "slices" may present the enhanced data without thresholding, thereby displaying enhanced features against an otherwise opaque background.

In the present invention, additional displays are used to illustrate individual singular vectors, or sets of singular vectors. Other displays are used to illustrate the frequency spectra of the singular vectors, or in the case of the right singular vectors, spectrogram displays.

In alternative embodiments, a "movie" time history of data received for each time interval is displayed by thresholding and rapidly expanding the compressed data into its full, three-dimensional form and displaying the data in a time sequence within an evolving, transparent data cube. Furthermore, as new data is added to the top of the data cube, older time history data is dropped off the bottom of the data cube.

In an alternative embodiment, a movie display of enhanced data against an opaque background may be displayed as if one were rapidly "slicing" through the data cube.

While the foregoing invention has been described with reference to particular embodiments, it should be understood that various modifications and alterations will occur to those skilled in the art. Such modifications and alterations are intended to fall within the scope of the appended claims. Such modifications and alterations include implementing the invention with other multivariate data, including RF data, seismic data, and various forms of communication data.

In view of the foregoing, I claim:

1. A method of enhancing medical signals received from a monitoring device comprising the steps of:

inputting medical signals:

extracting data from said medical signals;

embedding said data into a data matrix;

compressing said data matrix into a compressed-data-form;

formatting a portion of said compressed-data-form into at least one auto-correlation matrix;

determining the structural characteristics of each said autocorrelation matrix;

filtering said compressed-data-form based on said structural characteristics to form a filtered compressed-data-form; and expanding selected data values in said filtered compressed-data-form to result in enhanced data.

2. The method of claim 1, further comprising the step of displaying said enhanced data on a display screen wherein said display shows features of interest in said medical signal.

3. The method of claim 1, further comprising the step of modifying selected data values in said compressed-data-form.

4. The method of claim 3, said compressing step further including decomposing said data matrix into first singular vectors and first singular values.

5. The method of claim 4, wherein at least one said first singular vector is modified by said modifying step.

6. The method of claim 4, wherein at least one said first singular value is modified by said modifying step.

7. The method of claim 4 wherein said formatting step further includes:

transforming at least one said first singular vector into a set of frequency domain coefficients;

multiplying each said coefficient by a complex conjugate;

transforming each coefficient into a set of time domain coefficients; and placing said time domain coefficients in a Toeplitz matrix form.

8. The method of claim 7 further comprising weighting said combined selected second singular vectors by said corresponding second singular values.

9. The method of claim 3 wherein said method further includes modifying said data matrix by multiplying at least a portion of said data matrix by a singular vector.

10. The method of claim 3 wherein said method further includes partitioning said compressed-data-form into subspaces.

11. The method of claim 10 wherein said compressed-data-form is partitioned into subspaces on the basis of said singular values.

12. The method of claim 11, said method including the step of saving at least one subspace of said compressed-data-form in a historical database.

13. The method of claim 1, said method including the step of saving at least a portion of said compressed-data-form in a historical database.

14. The method of claim 13, said method including the step of concatenating said historical database with said data matrix before compressing said data matrix.

15. The method of claim 13, said method including the step of concatenating said historical database with said compressed-matrix-form after compressing said data matrix.

16. The method of claim 13 wherein said method further includes modifying said historical database before saving said database.

17. The method of claim 1 including the step of concatenating a medical data model with said data matrix before compressing said data matrix.

18. The method of claim 17 wherein said medical data model comprises compressed data.

19. The method of claim 1 including the step of concatenating a medical data model with said data matrix after compressing said data matrix.

20. The method of claim 19 wherein said medical data model comprises compressed data.

21. The method of claim 1, said compressing step further including decomposing said data matrix into eigenvectors and eigenvalues.

22. The method of claim 1 wherein said method further includes scaling said information in said data matrix by multiplying said information at a selected location in said data matrix by a data coefficient associated with said location.

23. The method of claim 1, said determining step further comprising decomposing said autocorrelation matrix into second singular vectors and second singular values.

24. The method of claim 23 further comprising the step of filtering said first singular vectors by said second singular vectors to result in filtered singular vectors.

25. The method of claim 24, said expanding step further comprising combining selected second singular vectors together to form enhanced singular vectors.

26. A method of compressing and storing medical data for later retrieval, comprising:

inputting medical signals:

extracting data from said medical signals;

embedding said data into a data matrix;

compressing said data matrix into a compressed-data-form;

formatting said data matrix into a compressed-data-form into at least one autocorrelation matrix;

determining the structural characteristics of each said autocorrelation matrix;

filtering said compressed-data-form based on said structural characteristics to form a filtered compressed-data-form;

saving selected data values in said filtered compressed-data-form in a computer-readable format.

27. A system for enhancing medical signals received from a monitoring device comprising:

extractor for extracting data from medical signals;

embedder for embedding said data into a data matrix;

compressor for compressing said data matrix into a first compressed-data-form;

formatter for formatting a portion of said first compressed-data-form into at least one autocorrelation matrix;

means for determining the structural characteristics of each said autocorrelation matrix;

filter for filtering said first compressed-data-form based on said structural characteristics to form a filtered first compressed-data-form; and expander for expanding selected data values in said filtered first compressed-data-form to result in enhanced data.

28. The system of claim 27, further comprising a display system for displaying said enhanced data with the display system including a display screen that is capable of displaying features of interest in said medical signals.

29. The system of claim 27, further comprising a first modifier for modifying selected data values in first compressed-data-form.

30. The system of claim 29, wherein said compressor further includes a decomposer for a decomposing said data matrix into first singular vectors and first singular values.

31. The system of claim 30, wherein at least one said first singular vector is modified by said modifier first.

32. The system of claim 30, wherein at least one said first singular value is modified by said modifier first.

33. The system of claim 29, wherein said system further includes a third modifier for modifying said data matrix by multiplying at least a portion of said data matrix by a singular vector.

34. The system of claim 29, wherein said system further includes a partitioner for partitioning said first compressed-data-form into subspaces.

35. The system of claim 34, wherein the partitioner partitions said compressed-data-form into subspaces on the basis of said singular values.

36. The system of claim 35, wherein said system includes storage means which stores at least one subspace of said first compressed-data-form in a historical database.

37. The system of claim 27, wherein said system includes storage means which stores at least a portion of said first compressed-data-form in a historical database.

38. The system of claim 37, wherein said system includes concatenating means for concatenating said historical database with said data matrix before the compressor compresses said data matrix.

39. The system of claim 37, said system includes concatenating means for concatenating said historical database with said first compressed-matrix-form after the compressor compresses said data matrix.

40. The system of claim 37 wherein said system further includes a second modifier means said historical database before storing said database.

41. The system of claim 27, wherein the includes concatenating means concatenates a medical data model with said data matrix before the compressor compresses said data matrix.

42. The system of claim 41, wherein said medical data model comprises compressed data.

43. The system of claim 27, wherein the system includes concatenating means which concatenates a medical data model with said data matrix after the compressor compresses said data matrix.

44. The system of claim 43, wherein said medical data model comprises compressed data.

45. The system of claim 27, wherein said compressor further includes a decomposer for decomposing said data matrix into eigenvectors and eigenvalues.

46. The system of claim 27, wherein said system further includes a scalar for scaling said information in said data matrix by multiplying said information at a selected location in said data matrix by a data coefficient associated with said location.

47. The system of claim 27, wherein said means for determining further compresses a decompressor for decomposing said autocorrelation matrix into second singular vectors and second singular values.

48. The system of claim 47, wherein the system further includes second filter means for filtering said first singular vectors by said second singular vectors to result in filtered singular vectors.

49. The system of claim 48, wherein the expander further includes a combiner for combining selected second singular vectors to form enhanced singular vectors.

50. A system for compressing and saving medical data for later retrieval, comprising:

extraction for extracting data from medical signals;

embedder for embedding said data into a data matrix;

compressor for compressing said data matrix into a compressed- data-form;

formatter for formatting a portion of said compressed-data-form into at least one autocorrelation matrix;

means for determining the structural characteristics of each said autocorrelation matrix;

filter for filtering said compressed-data-form based on said structural characteristics to form a filtered compressed-data-form;

storage means for storing selected data values in said filtered compressed-data-form in a computer-readable format.

* * * * *